(12) United States Patent
Walfridsson et al.

(10) Patent No.: US 6,413,765 B1
(45) Date of Patent: Jul. 2, 2002

(54) GENETICALLY MODIFIED LACTIC ACID BACTERIA HAVING MODIFIED DIACETYL REDUCTASE ACTIVITIES

(75) Inventors: Mats Walfridsson, Lund (SE); Claus Maxel Henriksen, Copenhagen; Dan Nilsson, Espergaerde, both of (DK)

(73) Assignee: Chr. Hanson A/S, Hoersholm (DK)

( * ) Notice: Subject to any disclaimer, the term of this patent is extended or adjusted under 35 U.S.C. 154(b) by 0 days.

(21) Appl. No.: 09/295,445

(22) Filed: Apr. 21, 1999

Related U.S. Application Data

(60) Provisional application No. 60/082,566, filed on Apr. 21, 1998.

(51) Int. Cl.⁷ ................................................. C12N 1/20
(52) U.S. Cl. ................... 435/252.9; 435/189; 435/190; 435/252.1; 435/440; 435/441; 435/448
(58) Field of Search .............................. 435/252.3, 189, 435/190, 252.1, 440, 252.9, 441, 448

(56) References Cited

U.S. PATENT DOCUMENTS 4,938,973 A * 7/1990 Klaver et al. ................. 426/42

FOREIGN PATENT DOCUMENTS

EP          0 199 105        10/1986

OTHER PUBLICATIONS

Cowell, I.G. and Austin, C. A. cDNA Library Protocols. NJ: Humana Press Inc., 1997.*
Ables, R.H., Frey, P.A., Jencks, W.P. Biochemistry. MA: Jones and Bartlett Publishers, 1992.*
Salminen, S. and von Wright, A. Lactic acid bacteria:microbiology and functional aspects. NY: Marcel Dekker, inc, Mar. 27, 1998.*
Arora, B.C., Dutta, S.M., Sabharwal, V.B., and Ranganathan, B. Mutants of Streptococcus lacits subsp. diacetylactis lacking diacetyl reductase activity. Acta Microbiologica Polonica. 27(4): 353–358, 1976, 1978.*
Cogan, T. Constitutive nature of the enzymes of citrate metabolism in Streptococcus lactis subsp. diactylactis. J. Dairy Research 48: 489–495, 1981.*
Steinbuchel, A. and Schlegel, H.G. A multifunctional fermentative alcohol dehydrogenase from the strict aerobe alcaligenes eutrophus: purification and properties. Eur. J. Biochem. 141: 555–564, 1984.*
Stiels, M. E. nd Holzapfel, W.H. Lactic acid bacteria of foods and their current taxonomy. Int. J. Food Microbiol. 36:1–29, 1997.*
Khrebtukova, I. and Spreitzer, R.J. Elimination of the Chlamydomoas gene family that encodes the small subunit of ribulose–1,5–bisphosphate carboxylase/oxygenase. Proc. Natl. Acad. Sci. USA 93:13689–13693, 1996.*
GenBank Accession AAA19188, Jun. 23, 1994*
GenBank Accession CAB14949, Nov. 1997.*
GenBank Accession L31844, Sep. 1994.*
GenBank Accession 1093520, Jul. 1992.*
GenBank Accession AAB58982, Jun. 1997.*
GenBank Accession AAC48769, Oct. 1997.*
Mellerick, Dervla and Timothy Cogan, "Induction of some enzymes of citrate metabolism in Leuconostoc lactis and other heterofermentative lactic acid bacteria<" *Journal of Dairy Research,* (1981), 48: 497–502.
Aungpraphapornchai, Prawat, Hugh G. Griffin, and Michael J. Gasson, "Cloning, DNA Sequence Analysis, and Deletion of a Gene Encoding Diacetyl–Acetoin Reductase from lactococcus lactis," *DNA Sequence,* 1999, vol. 10(3), pp. 1630172.
Jeroen Hugenholtz and Marjo J.C. Starrenburg, "Diacetyl production by different strains of Lactococcus lactis subsp. Lactis var. diacetylactis and Leuconostoc spp." *Appl. Microbiol Biotechnol* (1992) 38: 17–22.
E.W. Seitz, W.E. Sandine, P.R. Elliker and E.A. Day, "Distribution of Diacetyl Reductase Among Bacteria," Department of Microbiology and Food Science and Technology, Oregon State University Corvallis, 186–189.
Ana Ramos, Juke S. Lolkema, Wil N. Konings, and Helena Santos, "Enzyme Basis for pH Regulation of Citrate and Pyruvate Metabolism by Leuconostoc oenos," *Applied and Environmental Microbiology,* Apr. 1995, p. 1303–1310.
Jeroen Hugenholtz, "Citrate metabolism in lactic acid bacteria," *FEMS Microbiology Reviews* 12 (1993) 165–178, 1993.
Jakubowska, J., et al., "Evaluation of Lactic Acid Streptococci for the Preparation of Frozen Concentrated Starter Cultures," ACTA Microbiologica Polonica, vol. 29, No. 2, pp. 135–144 (1980).
Arora, B.C., et al., "Mutants of *Streptococcus lactis* subsp. diacetylactis Lacking Diacetyl Reductase Activity," ACTA Microbiologica Polonica, vol. 27, No. 4, pp. 353–358 (1976).
Boumerdassi, H., et al., "Isolation and Properties of *Lactococcus lactis* subsp. lactis biovar diacetylactis CNRZ 483 Mutants Producing Diacetyl and Acetoin from Glucose," Applied and Environmental Microbiology, vol. 63, No. 6, pp. 2293–2299 (Jun., 1997).

(List continued on next page.)

*Primary Examiner*—Nashaat T. Nashed
*Assistant Examiner*—Christian L. Fronda
(74) *Attorney, Agent, or Firm*—Foley & Lardner

(57) ABSTRACT

Genetically modified lactic acid bacteria having a reduced or lacking or enhanced diacetyl reductase activity, acetoin reductase activity and/or butanediol dehydrogenase activity are provided. Such bacteria are used in starter cultures in the production of food products including dairy products where it is desired to have a high content of diacetyl and for reducing or completely removing diacetyl in beverages including beers, fruit juices and certain types of wine, where the presence of diacetyl is undesired.

16 Claims, 4 Drawing Sheets

OTHER PUBLICATIONS

Figure 1A:
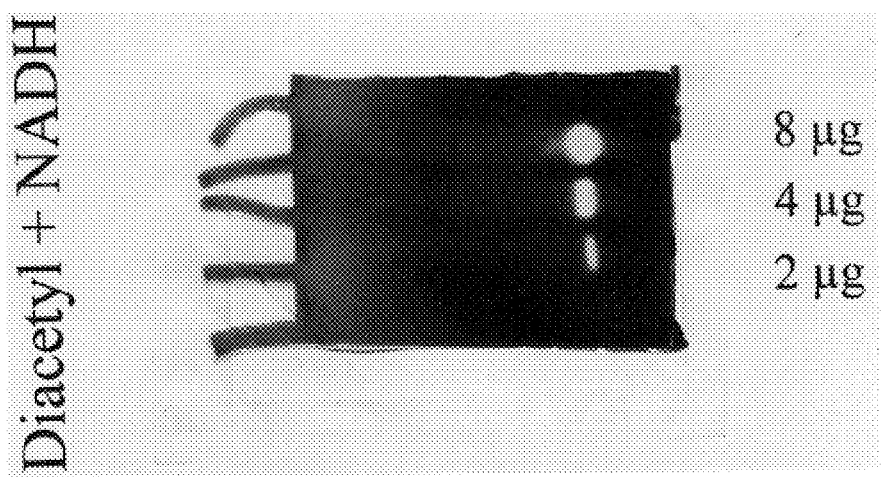

Crow, V., "Properties of 2,3–Butanediol Dehydrogenases from *Lactococcus lactis* subsp. lactis in Relation to Citrate Fermentation," Applied and Environmental Microbiology, vol. 56, No. 6, pp. 1656–1665 (Jun. 1990).

Curic, M., et al., "A General Method for Selection of a α–Acetolactate Decarboxylase–Deficient *Lactococcus lactis* Mutants to Improve Diacetyl Formation," Applied and Environmental Microbiology, vol. 65, No. 3, pp. 1202–1206 (Mar., 1999).

Dickely, F., et al., "Isolation of *Lactococcus lactis* Nonsense Suppressors and Construction of a Food–Grade Cloning Vector," Molecular Microbiology, vol. 15, No. 5, pp. 839–847 (1995).

Gibson, T., et al.,"Purification and Characterization of Diacetyl Reductase from Chicken Liver and *Streptococcus lactis* and Enzymic Determination of Diacetyl and Diketones," Enzyme Microbiology Technology, vol. 13, pp. 171–178 (Feb. 1991).

Giovannini, P., et al., "Properties of Diacetyl (Acetoin) Reductase from *Bacillus Stearothermophilus*," Biorganic & Medicinal Chemistry, vol. 8, No. 4, pp. 1197–1201 (1996).

Kuila, R.K., et al., "Ultraviolet Light–Induced Mutants of *Streptococcus lactis* Subspecies diacetylactis with Enhanced Acid or Flavor–Producing Abilities," Journal of Dairy Science, vol. 61, pp. 379–383 (1978).

Povecho, P., et al., "Further Purification and Characterization of Dicetyl Reducing Enzymes from Beef Liver," International Journal of Biochemistry, vol. 16, pp. 423–427 (1984).

Richelieu, M., et al., "Determination of α–Acetolactic Acid and Volatile Compounds by Headspace Gas Chromatography," Journal of Dairy Science, vol. 80, pp. 1918–1925 (1997).

Terzaghi, B., et al., "Improved Medium for Lactic Streptococci and Their Bacteriophages," Applied Microbiology, vol. 29, No. 6, pp. 807–813 (Jun., 1995).

* cited by examiner

Diacetyl + NADH

8 µg
4 µg
2 µg

Butanediol + NAD⁺

8 µg
4 µg
2 µg

Acetoin + NADH

8 µg
4 µg
2 µg

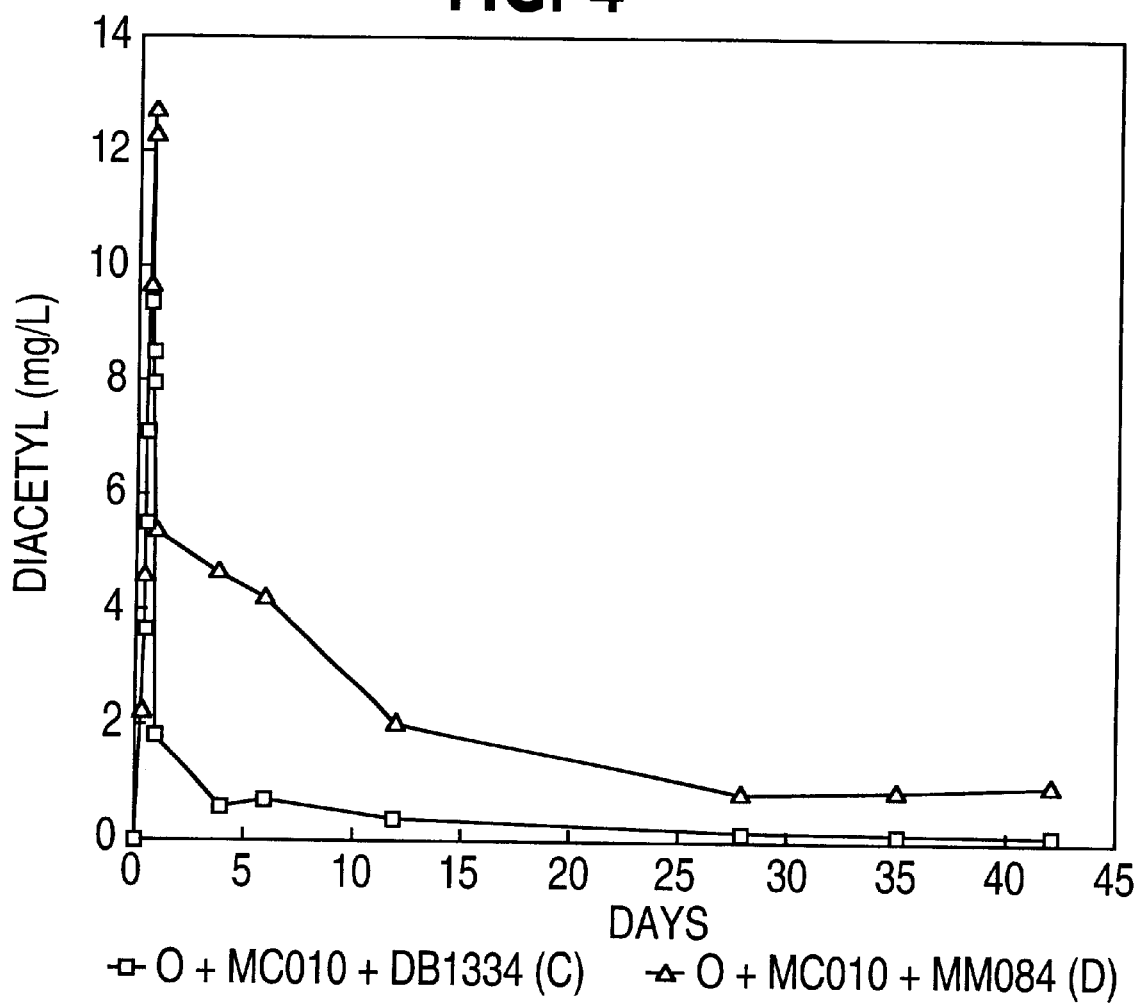

GENETICALLY MODIFIED LACTIC ACID BACTERIA HAVING MODIFIED DIACETYL REDUCTASE ACTIVITIES

This Appln claims benefit of Provisional No: 60/082,566 filed Apr. 21, 1998.

FIELD OF THE INVENTION

The present invention relates to the field of manufacturing food products by means of lactic acid bacterial cultures. Specifically the invention provides novel genetically modified strains of lactic acid bacteria that are modified to have enhanced or reduced diacetyl reductase activity, acetoin reductase activity and/or butanediol dehydrogenase activity. Such modified bacteria are particularly useful in the manufacturing of food products having either a reduced or an increased content of the flavour compound diacetyl.

TECHNICAL BACKGROUND AND PRIOR ART

Lactic acid bacteria are used extensively as starter cultures in the food industry in the manufacturing of fermented products including milk products such as e.g. yoghurt and cheese, meat products, bakery products, wine and vegetable products. Lactococcus species including *Lactococcus latcis* are among the most commonly used lactic acid bacteria in dairy starter cultures. Several other lactic acid bacteria such as Leuconostoc species, Pidococcus species. Lactobacillus species, Oenococcus species and Streptococcus species are also commonly used in food cultures.

When a lactic acid bacterial starter culture is added to milk or any other food product starting material under appropriate conditions, the bacteria grow rapidly with concomitant conversion of citrate, lactose or other sugar compounds into lactic acid/lactate and possibly other acids including acetate, resulting in a pH decrease. In addition, several other metabolites are produced during the growth of lactic acid bacteria. These metabolites include ethanol, formate, acetaldehyde, α-acetolactate, acetoin, diacetyl, carbon dioxide and 2,3 butylene glycol (butanediol).

Among these metabolites, diecetyl (2,3-butanedione) is an essential flavour compound in dairy products such as butter, yoghurt, starter distilate, margarine, buttermilk and cheese. However, its presence in other products, such as fruit juices, beers and wines, is undesirable, as it imparts a buttery or toffee taste and is the agent responsible for the so-called sarcina sickness of beer. The compound is formed during fermentation of lactic acid bacterial species of e.g. Lactococcus, Leuconostc and Lactobacillus by an oxidative decarboxylation of α-acetolactate which is formed from two molecules of pyruvate by the action of α-acetolactate synthase (ALS)

Diacetyl reducing enzymes, commonly termed diacetyl reducteses (DR) (acetoin:NAD oxidoreductases E. C. 1.1.1.5), have been observed from many different sources, notably animal tissues (Provecho et al., 1984), bacteria including Lactococcus (formerly *Streptococcus*) *lactis* (Crow, 1990; Arora et al., 1978), Bacillus species and Enterbacter species (Giovannini et al. 1996), and yeast (Gibson et al., 1991). Boumerdassi et al. 1997 disclosed a mutated *Lactococcus latis* strain having DR activity that was increased by three times relative to the activity of the parent strain. In Arora et al. 1978 and Kulia & Rangenathan 1978 are disclosed mutants of *Lactococcus lactis* having a reduced diacetyl activity when grown in non fat dry milk and citrate medium, respectively.

Generally, the term "discetyl reductase" ("DR") encompasses several enzymatic activities such as diacetyl reductase activity, acetoin reductese activity and/or butanediol dehydrogenase activity which carry out the following enzymatic reactions; diacetyl+NAD(P)H--->acetoin+NAD(P)$^+$, acetoin+NAD(P)H<--->butanediol+NAD(P)$^+$, respectively. Thus, *L. lactis* has been reported to possess two diacetyl reductases with activity for both diacetyl and acetoin. Both of these enzymes use NADH as cofactor (Crow, 1990).

Leuconostoc species including *Leu. pseudomesenteroides* are typically used in mixed starter cultures together with *Lactococcus lactis* subsp. *lactis* and *Lactococcus lactis* subsp. *lactis* biovar. *diacetylactis* in the production of dairy products. A significant role of Leuconostoc species in such mixed cultures is to remove the acetaldehyde produced by the accompanying strains e.g. in the production of buttermilk and fresh cheeses. However, Leuconostoc strains will also remove diacetyl by reducing it into acetoin and/or butanediol, a characteristic that is generally undesirable in the production of dairy products. The enzyme responsible for the reduction of diacetyl, diacetyl reductase, is highly expressed in Leuconostoc species such as *Leu. psoudomesenteriodes* which species is known to have about 100 times higher diacetyl reductese activity than *L. lactis*.

Thus, one primary objective of the present invention is to provide lactic acid bacterial cultures of species, including Leuconastoc species, that inherently have one or more DR activities which, relative to the naturally occurring strains, has reduced or substantially eliminated DR activities under specific cofactor conditions. By providing such strains to the industry, it has become possible to produce lactic acid bacterial fermented food products having a desirably high content of diacetyl.

Another objective of the invention is to provide lactic acid bacterial strain that, relative to the presently available strains, has a strongly enhanced DR activities. Using such strains which utilise diacetyl as a substrate it is possible to reduce or remove diacetyl in food products where the presence of this flavour compound is undesirable.

SUMMARY OF THE INVENTION

Accordingly, the invention provides in a first aspect a genetically modified lactic acid bacterium, including the *Leuconostoc pseudomesenteroides* strains DSM 12099 and DSM 12465 and lactic acid bacteria essentially having the diacetyl reductase characteristics of these strains, that, relative to the lactic acid bacterium from which it is derived, is modified to have a reduction of at least one of diacetyl reductase activity, acetoin reductase activity and butanediol dehydrogenase activity, said modified bacterium, (i) is substantially incapable of at least one of diacetyl reductase activity and acetoin reductase activity in a medium containing NADH and not containing NADPH, or (ii) is substantially incapable of at least one of diacetyl reductase activity and acetoin reductase activity in a medium containing NADPH and not containing NADH, or (iii) is substantially incapable of at least one of diacetyl reductase activity and acetoin reductase activity in a medium containing both NADH and NADPH, or (iv) is substantially incapable of butanediol dehydrogenase activity in a medium containing NAD$^+$ and not containing NADP$^+$, or (v) is substantially incapable of butanediol dehydrogenase activity in a medium containing NADP$^+$ and not containing NAD$^+$, or (vi) is substantially incapable of butanediol dehydrogenase activity in a medium containing both NAD$^+$ and NADP$^+$, where the bacterium prior to being modified is capable of having at least one of said enzymatic activities under said cofactor conditions.

In a further aspect, the invention relates to a genetically modified lactic acid bacterium that, relative to the lactic acid bacterium from which it is derived, is modified to have a reduction of at least one of diacetyl reductase activity, acetoin reductase activity and butanediol dehydrogenase activity, including the *Leuconostoc pseudomesenteroides* strains DSM 12099 and DSM 12465 and lactic acid bacteria essentially having the diacetyl reductase characteristics of these strains, subject to the limitation, that the lactic acid bacterium is not *Lactococcus lactis*.

In a still further aspect, the invention relates to a genetically modified lactic acid bacterium that has no detectable diacetyl reductase activity, acetoin reductase activity and/or butanediol dehydrogenase activity, subject to the limitation, that the lactic acid bacterium is not *Lactococcus lactis*.

In other further aspects, the invention relates to a genetically modified lactic acid bacterium that, relative to the lactic acid bacterium from which it is derived, is modified to have an enhancement of at least one of diacetyl reductase activity, acetoin reductase activity and butanediol dehydrogenase activity which is at least 10 times, including the *Lactococcus lactis* subsp, *lactis* strain DSM 12096 and lactic acid bacteria essentially having the diacetyl reductase characteristics of that strain.

In a still further aspect, the invention pertains to a starter culture composition comprising such a genetically modified bacterium.

There is also provided a method of preparing a fermented food product, comprising adding an effective amount of a bacterium that, relative to the lactic acid bacterium from which it is derived, is modified to have a reduction of at least one of diacetyl reductase activity, acetoin reductase activity and butanediol dehydrogenase activity, or a composition comprising such a bacterium to a food product starting material wherein the bacterium or the composition is incapable of having at least one enzymatic activity selected from the group consisting of diacetyl reductase activity, acetoin reductase activity and butanediol dehydrogenase activity and keeping the starting material under conditions where the bacterium or the starter culture composition is capable of fermenting said starting material to obtain the fermented food, and a fermented food product obtainable by such a method which product has a content of discetyl which is at least 10% higher than that of a product fermented under identical conditions with a parent strain for the genetically modified bacterium.

In yet another aspect, the invention relates to a method of producing a food product, comprising adding an effective amount of a bacterium that, relative to the lactic acid bacterium from which it is derived, is modified to have an enhancement of at least one of diacetyl reductase activity, acetoin reductase activity and butanediol dehydrogenase activity, or a composition comprising such a bacterium to a food product starting material that contains at least one of diacetyl, acetoin and butanediol, and keeping the starting material under conditions where the genetically modified lactic acid bacterium has at least one enzymatic activity selected from the group consisting of diacetyl reductase activity, acetoin reductase activity and butanediol dehydrogenase activity to obtain a product having a reduced content of diacetyl.

DETAILED DISCLOSURE OF THE INVENTION

It is, as it is mentioned above, an important objective of the present invention to provide lactic acid bacteria that has a reduced capability to convert diacetyl in a fermented food product to acetoin and/or butanediol. Accordingly, in one aspect the genetically modified lactic acid bacterium is a bacterium that, relative to the lactic acid bacterium from which it is derived, is modified so as to have a reduction of at least one of diacetyl reductase activity, acetoin reductase activity and butanediol dehydrogenase activity, said bacterium, when grown under at least one of the above cofactor conditions, where the bacterium prior to being mutated is capable of having at least one of said enzymatic activities, is substantially incapable of at least one of said activities. As used herein, the term "substantially incapable" indicates that the respective enzymatic activities can not be detected by the assay procedures described herein.

As used herein, the expression "lactic acid bacterium" refers to a group of gram-positive, microaerophilic or anaerobic bacteria having in common the ability to ferment sugars and citrate with the production of acids including lactic acid as the predominantly produced acid, acetic acid, formic acid and propionic acid. The industrially most useful lactic acid bacteria are found among Lactococcus species, Streptococcus species, Lactobacillus species, Leuconostoc species, Oenococcus species and Pediococcus species. In the dairy industry, the strict anaerobes belonging to the genus Bifidobacterium is generally included in the group of lactic acid bacteria as these organisms also produce lactic acid and are used as starter cultures in the production of dairy products.

It will be appreciated that the term "genetically modified" as used herein indicates any modification of DNA sequences coding for genes involved in the expression of DR activities including modifications of sequences that regulate the expression of genes coding for such enzymatic activities. Accordingly, genetic modification can be based on construction or selection of mutants of lactic acid bacteria or it can be based on recombinant DNA-technology. When the term "diacetyl reductase" or "DR" is used herein it refers to any of the three mentioned specific activities, i.e. diacetyl reductase activity, acetoin reductase activity and butanediol dehydrogenase activity.

As used herein the term "mutant" is used in the conventional meaning of that term i.e. it refers to strains obtained by subjecting a lactic acid bacterial strain to any conventionally used mutagenization treatment including treatment with a chemical mutagen such as ethanemethane sulphonate (EMS) or N-methyl-N'-nitro-N-nitroguanidine (NTG), UV light or to spontaneously occurring mutants which are selected on the basis of a modified DR activity. Although it is presently preferred to provide the genetically modified bacteria according to the invention by random mutagenesis or by selection of spontaneously occurring mutants, i.e. without the use of recombinant DNA-technology, it is envisaged that mutants of lactic acid bacteria can be provided by such technology including site-directed mutagenesis and PCR techniques and other in vitro or in vivo modifications of DNA sequences coding for DR activities or sequences regulating the expression of genes coding for the DR activities, once such sequences have been identified and isolated.

It is also possible to construct genetically modified bacteria according to the invention by conventional recombinant DNA-technology including insertion of sequences coding for DR activities, e.g. by replacing a native promoter for such coding sequences by a foreign promoter which either enhances or reduces the expression of the coding sequences. It is also possible to derive lactic acid bacterial strains according to the invention from species that do not have an inherent capability to produce DR activities by inserting genes coding for such activities isolated from a different organism comprising such genes. The source of such genes may be bacterial species, yeast species or mammal species. Additionally, it is envisaged that genetically modified bacteria according to the invention can be constructed by modifying metabolic pathways in a lactic acid bacterium that are not directly involved in DR pathways. It will be appreciated that the expression "under cofactor conditions" as used herein indicates the absence/presence in an appropriate medium of any non-protein substance required for biological activity of any of the enzyme activities according to the invention, such as $NAD^+$, NADH, $NADP^+$ and NADPH.

A genetically modified bacterium having a reduced diacetyl activity can be selected from any kind of lactic acid bacterial species which has an inherent DR activity, including Lactococcus spp., Streptococcus spp., Lactobacillus spp., Leuconostoc spp such as *Leuconostoc pseudomesenteroides*, Pediococcus spp., Oenococcus spp, and Bifidobacterium spp.

As mentioned above, the invention relates in another aspect to a genetically modified lactic acid bacterium that, relative to the lactic acid bacterium from which it is derived, is modified to have a reduction of at least one of diacetyl reductase activity, acetoin reductase activity and butanediol dehydrogenase activity, including the *Leuconostoc pseudomesenteroides* strains DSM 12099 and DSM 12465 and lactic acid bacteria essentially having the diacetyl reductase characteristics of these strains, subject to the limitation that the modified bacterium is not *Lactococcus lactis*.

However, in particularly useful embodiments, the above genetically modified bacterium is one that under cofactor conditions, where the bacterium prior to being genetically modified is capable of having at least one of diacetyl reductase activity, acetoin reductese activity and butanediol dehydrogenase activity, is substantially incapable of at least one of said enzymatic activities.

Such a bacterium includes a bacterium that is substantially incapable of at least one of diacetyl reductase activity and acetoin reductase activity in a medium containing NADH and not containing NADPH, a bacterium that is substantially incapable of at least one of diacetyl reductase activity and acetoin reductase activity in a medium containing NADPH and not containing NADH, a bacterium that is substantially incapable of at least one of diacetyl reductase activity and acetoin reductase activity in a medium containing both NADH and NADPH, a bacterium that is substantially incapable of butanediol dehydrogenase activity in a medium containing $NAD^+$ and not containing $NADP^+$, a bacterium that is substantially incapable of butanediol dehydrogenase activity in a medium containing $NADP^+$ and not containing $NAD^+$ and a bacterium that is substantially incapable of butanediol dehydrogenase activity in a medium containing both $NAD^+$ and $NADP^+$.

In a further aspect, the invention provides a genetically modified lactic acid bacterium that has no detectable diacetyl reductase activity, acetoin reductase activity and/or butanediol dehydrogenase activity. Such a bacterium is selected from any of the above-mentioned lactic acid bacterial species, subject to the limitation, that the bacterium is not *Lactococcus lactis*.

A genetically modified bacterium having reduced or no detectable DR activities can be derived from any lactic acid bacterial species which has an inherent DR activity, including Lactococcus spp. such as *Lactococcus lactis* subsp. *lactis* biovar. diacetylactis and *Lactococcus lactis* subsp. *lactis*, Streptococcus spp. including *Streptococcus thermophilus*, Lactobacillus spp., Leuconostoc spp. including *Leuconostoc pseudomesenteroides*., Pediococcus spp., Oenococcus spp. and Bifidobacterium spp.

Although it may be preferred that the modified bacterium has substantially no detectable DR activities, a bacterium that is modified to have a reduction of one or more of the above activities is also encompassed by the invention Thus, a useful bacterium according to the invention is one that has a reduction in any of the DR activities which, relative to the bacterium from which it is derived, is at least 25% such as at least 50% including at least 75% e.g. at least 90%. Thus, the genetically modified bacterium according to the invention preferably has a DR activity reduction which is reduced by at least 25 times for anyone of the enzymatic activities such as at least 50 times, including at least 100 times or even at least 500 times, relative to the strain from which it is derived.

When a modified lactic acid bacterial strain according to the invention is added to a food product starting material, such as e.g. milk, wherein the bacterium is incapable of having at least one of the above DR enzymatic activities and the starting material is kept under conditions where the strain is capable of fermenting said starting material to obtain a fermented food product, the resulting food product preferably has an increased content of diacetyl which is at least 1.1 times higher, such as at least 2 times higher, including at least 5 times higher or even at least 10 times higher, relative to a similar food product which is fermented using the strain from which the modified strain is derived.

Thus in one embodiment, the modified bacterium according to the invention is derived by subjecting a parent lactic acid bacterial strain that under appropriate cofactor conditions is capable of having diacetyl reductase activity, acetoin reductase activity and/or butanediol dehydrogenase activity to a mutagenization treatment and selecting a strain that is substantially incapable of at least one of said enzymatic activities under identical cofactor conditions.

The present invention relates in a further aspect to a genetically modified lactic acid bacterium that, relative to the lactic acid bacterium from which it is derived, is modified to have an enhancement of at least one of diacetyl reductase activity, acetoin reductase activity and butanediol dehydrogenase activity which is at least 10 times, including the *Lactococcus lactis* subsp. *lactis* strain DSM 12096 and lactic acid bacteria essentially having the diacetyl reductase characteristics of that strain.

It was found that it is possible to provide genetically modified lactic acid bacteria that have a significant enhancement of the specific DR activities. Thus, by fermenting a material or a medium having a content of diacetyl with such a genetically modified bacterium it is possible to obtain a final product wherein essentially all of the diacetyl has been converted to butanediol which is without the buttery flavour of diacetyl. Thus, the genetically modified bacterium according to the invention preferably has an activity enhancement which is at least 10 times for anyone of the enzymatic activities such as at least 50 times or even at least 100 times, relative to the strain from which it is derived.

A genetically modified bacterium having enhanced DR activities can be derived from any lactic acid bacterial species which has an inherent DR activity, including Lactococcus spp. such as *Lactococcus lactis* subsp. *lactis* biovar. *diacetylactis* and *Lactococcus lactis* subsp. *lactis*, Streptococcus spp. including *Streptococcus thermophilus*, Lactobacillus spp., Leuconostoc spp. including *Leuconostoc pseudomesenteroides*., Pediococcus spp. and Bifidobacterium spp.

It will be appreciated that such modified bacteria can be a spontaneous mutant or be provided by subjecting a lactic acid bacterium that has inherent DR activities to a mutagenization treatment as described above or by inactivating or deleting one or more genes involved in the expression of the DR activities using conventional recombinant DNA-technology.

The genetically modified bacteria according to the invention are useful as starter cultures in the production of food products. Accordingly, in a further important aspect, the invention relates to a starter culture composition comprising a bacterium according to the invention either having enhanced or a reduced or eliminated DR activities.

Typically, such a composition comprises the bacteria in a concentrated form including frozen, dried or freeze-dried concentrates typically having a concentration of viable cells which is in the range of $10^4$ to $10^{12}$ cfu per g including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e g. at least $10^{10}$ cfu/g, such as at least $10^{11}$ cfu/g of the composition. The composition may as further components contain cryoprotectants and/or conventional additives including nutrients such as yeast extract, sugars and vitamins.

As it is normal in the production of lactic acid bacterial fermentation processes to apply mixed cultures lactic acid bacteria, the composition will in certain embodiments comprise a multiplicity of strains either belonging to the same species or belonging to different species. A typical example of such a useful combination of lactic acid bacteria in a starter culture composition is a mixture of a Leuconostoc spp, and one or more Lactococcus spp. such as *Lactococcus lactis* subsp. *lactis* or *Lactococcus lactis* subsp. *lactis* biovar. *diacetylactis*. Such a mixed culture can be used in the manufacturing of fermented milk products such as buttermilk and cheese. It will be understood that in such a mixed culture of lactic acid bacteria, one or more of the strain components may be a modified bacterium according to the invention.

It is also an objective of the invention to provide a method of preparing a fermented food product based on the use of the genetically modified bacteria of the invention which have reduced or lacking DR activities. In its broadest aspect, such a method comprises that an effective amount of such bacteria or a composition comprising the bacteria are added to a food product starting material wherein the bacterium or the composition is incapable of having at least one of the above DR enzymatic activities and keeping the starting material under conditions where the bacterium or the culture composition is capable of fermenting said starting material to obtain a fermented food product.

Useful food product starting materials include any material which is conventionally subjected to a lactic acid bacterial fermentation step such as milk, vegetable materials, meat products, fruit juices, must, doughs and batters. The fermented products which are obtained by the method include as typical examples dairy products such as cheese including fresh cheese products, and buttermilk.

As it is mentioned above, the use in food starter cultures of bacteria according to the invention that have a reduced or lacking DR activity will result in final products having a content of the desired flavour compound diacetyl which is higher than would otherwise be obtained if a non-modified lactic acid bacterium was used. Accordingly, it is an important aspect of the invention to provide a fermented food product obtainable by the above method which product has a content of diacetyl which is at least 10% higher such as at least 20% higher or at least 30% higher than that of a product fermented under identical conditions with a parent strain for the genetically modified bacterium Examples of such food products include milk-based products such as cheese and buttermilk, vegetable products, meat products, fruit juices, wines and bakery products.

As shown in the below Examples, when the DR mutant MM084 is used as a component of a mixed flavour-forming starter culture for the fermentation of one of the above starting materials, the mutant has a significant effect on the diacetyl stability during storage of the resulting fermented product.

Thus, an advantageous feature of the fermented food product according to the invention is that the food product can be stored for several weeks with less reduction in the diacetyl content than is the case with a food product fermented under identical conditions with the parent strain of the genetically modified bacterium. Thus, in one particularly useful embodiment, the fermented product is one which at least 10% of its initial diacetyl content is retained after storage for 20 days of more at about 4° C. when stored under appropriate storage conditions, such as at least about 20% of its initial diacetyl content e.g. at least about 30% and preferably at least about 40% e.g. at least about 50% of its initial diacetyl content is retained after storage for 20 days or more at about 4° C. This improvement implies that a fermented food product manufactured by use of the above mixed starter culture can be stored for an extended period of time without loosing its desired flavour.

Whereas in many lactic acid bacterial fermented food products it is desirable to have a high content of diacetyl, this may be undesirable in other products. This is in particular the case in beverages such as fruit juices, beers and other yeast fermented beverages including certain wines, where diacetyl imparts to the products a buttery or toffee taste. In beers a diacetyl content above the threshold level gives rise to the so-called sarcina sickness. It is therefore an interesting aspect of the invention to provide a method of producing a food product having a reduced content of diacetyl.

This method comprises adding an effective amount of a lactic acid bacterium that has been modified to have at least one increased DR activity or a composition containing such a bacterium to a food product starting material that contains at least one of diacetyl, acetoin and butanediol, and keeping the starting material under conditions where the genetically modified lactic acid bacterium has at least one enzymatic activity selected from the group consisting of diacetyl reductase activity, acetoin reductase activity and butanediol dehydrogenase activity to obtain a product having a reduced content of diacetyl. In useful embodiments the products resulting from such a method have no detectable content of diacetyl.

Figure 1B:
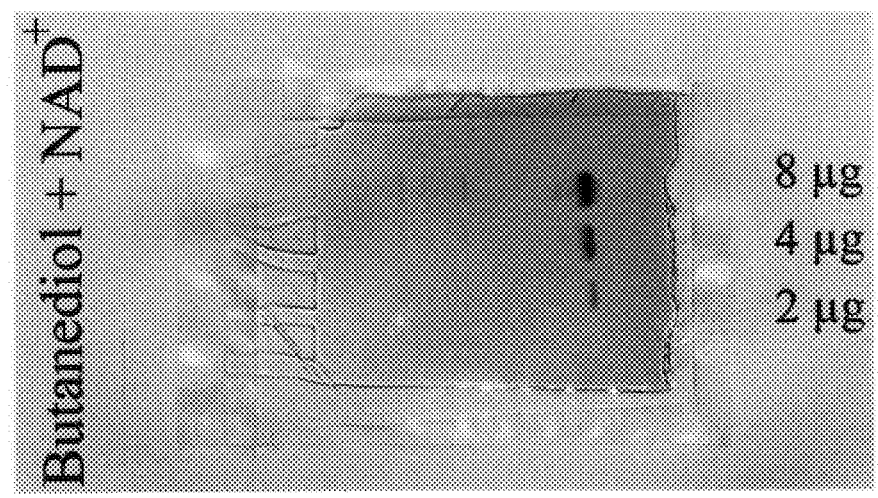
Figure 1C:
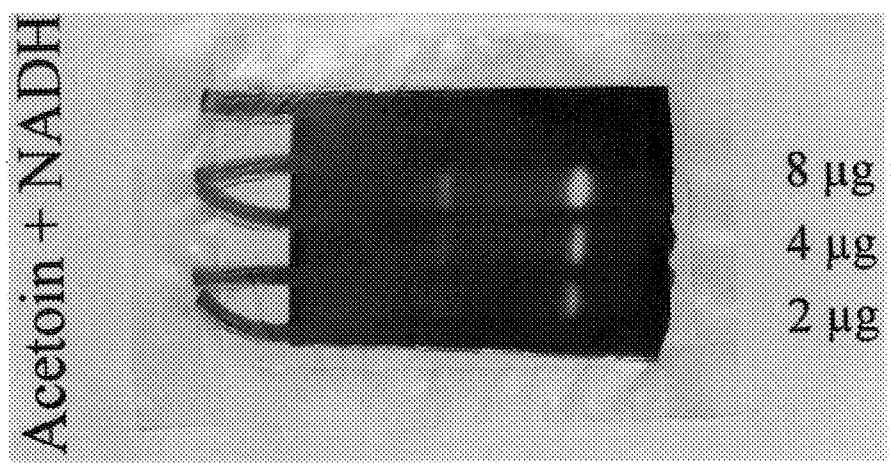
Figure 2A:
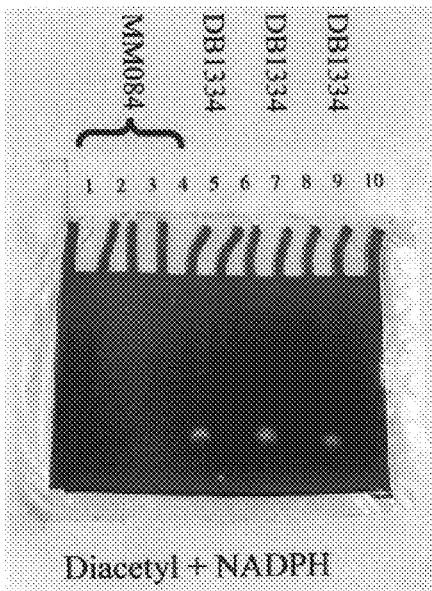
Figure 2B:
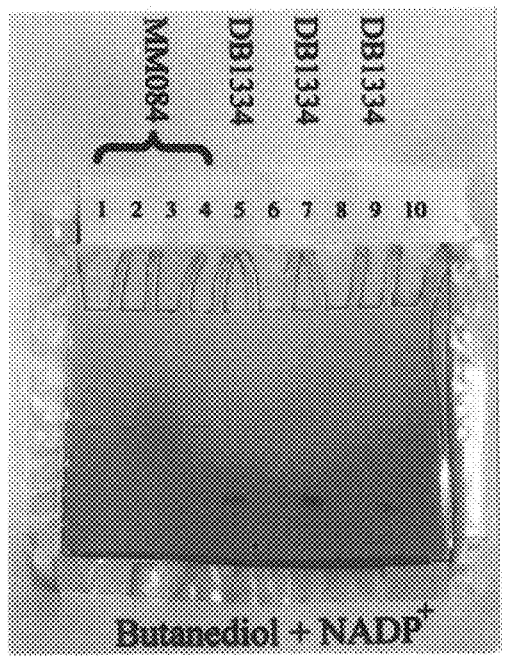

The invention will now be described in further details in the following non-limiting examples and the drawings wherein FIGS. 1A–1C show native-PAGE gels containing cell free extracts of wild-type strain of *Leu.pseudomesenteroids* DB1334. The gels were incubated with diacetyl+ NAD+(B); and acetoin+NADH(c), and stained with Meldola's blue and MTT. 2,4, and 8 μg of protein, respectively were loaded onto each gel;

FIGS. 2A and 2B show native-PAGE gels containing cell free extracts of wild-type strain of *Leu.pseudomesenteroides* DB1334 and mutant strain MMO84 strained with the zymogram technique. The gels were incubated with diacetyl + NADPH (A) or butanediol +NADP$^+$(B). MMO84 was laded in lanes 1–4 and DB1334 in lanes 5, 7 and 9. Approximately 6 μg of protein was loaded in each lane.

Figure 3:
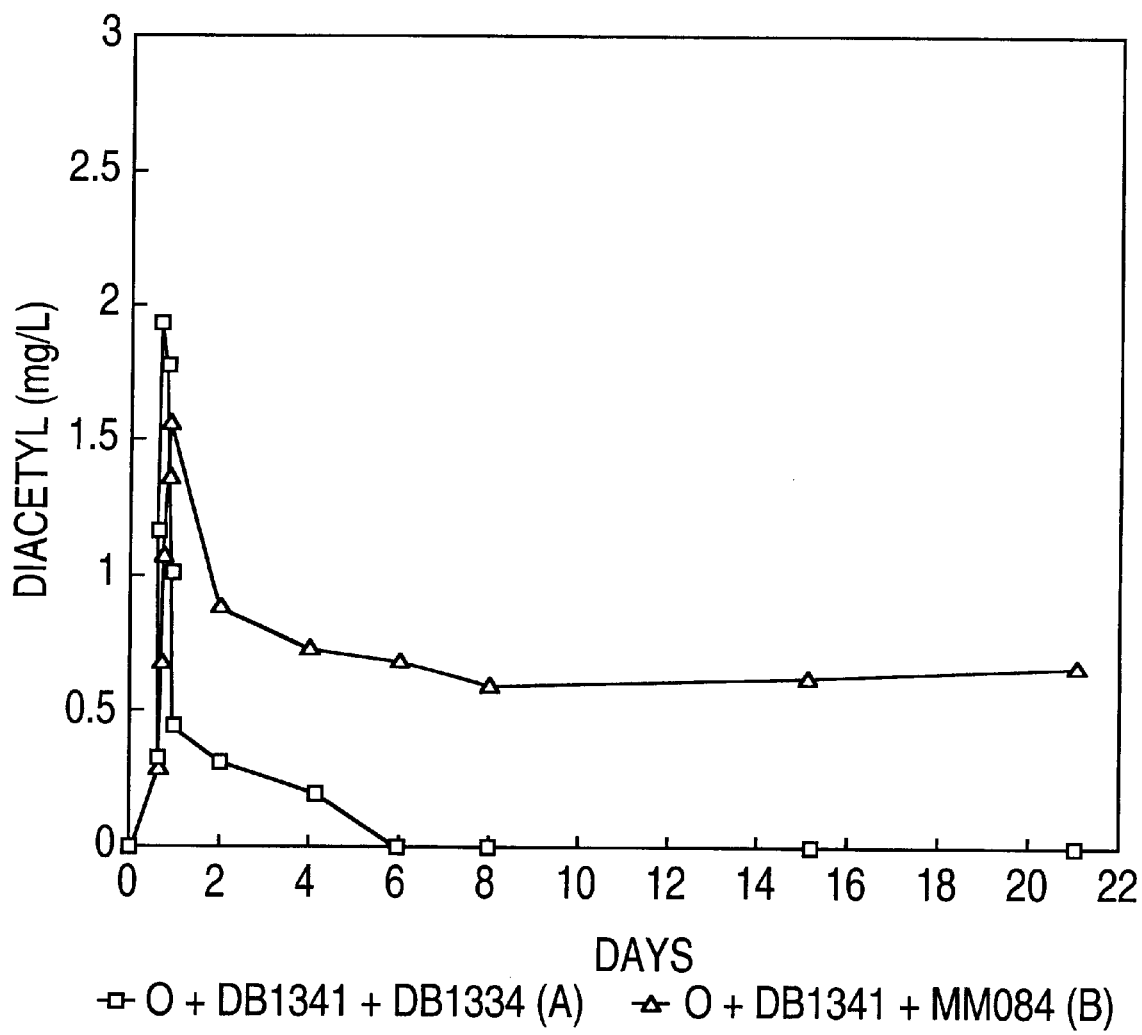

FIG. 3 illustrates the diacetyl content in reconstituted skimmed milk fermented by the mixed cultures A and B during fermentation and storage. The reconstituted skimmed milk was fermented at 22° C. in non-shaken bottles and subsequently stored at 4° C., and FIG. 4 illustrates the diacetyl content in sour cream fermented with the mixed cultures C and D during fermentation and storage. The cream was fermented at 22° C. and subsequently stored at 4° C.

EXAMPLE 1

Construction of a NADH-dependent Diecetyl Reductase Mutant of *Leuconostoc pseudomesenteroides*

1.1. Summary of Experiments

Partially purified NADH-dependent diacetyl reductase from *Leucanostoc pseudomesenteroides* showed that the enzyme is responsible for at least three enzymatic reactions (i) diacetyl+NADH--->acetoin+NAD$^+$; (ii) acetoin+ NADH--->butanediol+NAD$^{30}$ ; and (iii) butanediol+ NAD$^+$--->acetoin+NADH. The enzymatic properties of diacetyl reductase were demonstrated by staining native PAGE gels using the zymogram technique as described in the following. Using this technique, the immobilised enzyme is allowed to react with a substrate and cofactor with a subsequent dye staining. The same technique was also used to screen an ethanemethane sulphonate (EMS) mutagenized *Leu. pseudomesenteroides* population for the absence of diacetyl reductase (butanediol dehydrogenase activity) activity by direct staining of colonies immobilised onto nitrocellulose membranes. Enzyme activity measurements from cell extracts showed that the mutant possessed only minute diacetyl reductase activity, no acetoin reductase or butanediol dehydrogenase activity when reading with NADH or NAD$^+$. However activities comparable to the wild-type strain were obtained when using NADPH or NADP$^+$ as cofactors, indicating the presence of two distinct diacetyl reductases in *Leu. pseudomesenteroides*.

In this example, the isolation and characterization of a mutant strain of *Leu. pseudomesenteroides* that is defective with respect to an NADH-dependent diacetyl reductase is described.

1.2. Materials and Methods (i) Bacterial Strain

A wild-type strain of *Leu. pseudomesenteroides* DB1334 (Chr. Hansen Culture Collection (CHCC) 2114) was used in the experiment.

(ii) Cultivation Conditions

*Leu. pseudomesenteroides* was cultivated in M17 medium (Terzaghi & Sandine, 1975) supplemented with 0.5% glucose at 25° C. under anaerobic conditions.

(iii) Mutagenesis

*Leu. pseudomesenteroides* was cultivated in 10 ml M17 (0.5% glucose) for 3 days followed by cultivation for 120 minutes in the presence of 150 μl of EMS. After EMS treatment, 0.2 ml of the culture was inoculated into ten tubes each containing 10 ml of M17 and incubated for 3 days for phenotypic expression. The mutation frequency was monitored by plating 0.1 ml from each tube onto M17 plates containing 500 μg/ml of streptomycin.

(iv) Colony Screening for Mutants

Cells having been subjected to mutagenization were plated on M17 (0.5% glucose) and incubated anaerobically for 2 days at 25° C. and subsequently streaked onto duplicate M17 plates. After another 2 days of incubation one of the duplicate plates was used for screening. The colonies were transferred onto a nitrocellulose membrane and soaked for 1.5 minutes in chloroform for cell lysis. After cell lysis, the membrane was washed with distilled water and dried for 20 minutes. The membrane was next incubated for 30 minutes in a solution containing 0.5 M Na-phosphate buffer (pH 6.1), 72 mM butanediol, 1 mM NAD$^+$, 0.02 mM Meldola's blue (8-Dimethylamino-2,3-benzophenoxazine) 0.8 mM MTT (3-[4,5-Dimethylthiazol-2-yl] 2,5diphenytletrazolium bromide; Thiazolyl blue).

(v) Protein Electrophoreis

Using 4–20% Tris-HCl gradient gels with Tris-Glycine (pH 8.3) as running buffer, native-PAGE was run at 150 V for 2.5 hours. Staining of native gels was performed both with 0.25% Coomassie brilliant blue in 10% acetic acid and 40% methanol and with the zymogram technique (see below). SDS-PAGE was run using a 12% separation gel, 4% stacking gel and with Tris-Glycine (pH 8.3) as running buffer at 200 V for 45 minutes.

(vi) Zymogram Staining of Gels

Zymogram staining of native-PAGE gets for identification of diacetyl reductase activity and butanediol dehydrogenase activity was performed as follows: for diacetyl reductase activity the gel was incubated for 15 minutes with 12 mM diacetyl, 1.5 mM NADH, 0.5 M Na-phosphate buffer (pH 6.1) and for butanediol dehydrogenase activity the gel was incubated for 15 minutes with 72 mM butanediol, 1 mM NAD$^+$, 0.5 M Na-phosphate buffer. The gel was subsequently incubated for 30 minutes under dry conditions before the addition of a solution consisting of 0.02 mM Meldola's blue (8-Dimethylamino-2,3-benzophenoxazine) 0.8 mM MTT (3-[4,5-Dimethylthiazol-2-yl] 2,5-diphenyltetrazolium bromide; Thiazolyl blue) in 100 mM phosphate buffer (pH 8.2) (Provecho et al, 1984; Gibson et al, 1991). Visible bands appeared within 20 minutes.

(vii) Preparation of Cell Free Extracts *Leu. pseudomesenteroides* was cultivated in M17 (0.5% glucose). The cells were harvested in the exponential growth phase by centrifugation at 6000 rpm for 15 minutes and washed in cold 50 mM Ne-phosphate buffer (pH 6). The pellet was resuspended in cold 50 mM Na-phosphate buffer (pH 6) and sonicated for 3×2 minutes. The sonicated cell mixture was centrifuged at 6000 rpm for 15 min. and the supernatant was stored at −20° C. until analysed for protein content and enzymic activities.

(viii) Enzyme Activity Measurements

Diacetyl reductase activity was measured spectrophotometrically by monitoring the oxidation of NADH at 340 nm in a reaction mixture with the following composition: 50 mM Na-phosphate buffer (pH 6.1), 36 mM diacetyl and 0.5 mM NADH. Butanediol dehydrogenast activity was measured by monitoring the reduction of NAD$^+$ at 340 nm in a reaction mixture with the following composition: 50 mM phosphate buffer (pH 6.1), 72 mM butanediol and 1 mM NAD$^+$. Acetoin reductase activity was measured by monitoring the oxidation of NADH at 340 nm in a reaction mixture with the following composition: 50 mM Na-phosphate buffer (pH 6.1), 36 mM acetoin and 0.5 mM NADH.

Lactate dehydrogenase was measured by monitoring the oxidation of NADH at 340 nm in a reaction mixture with the following composition: 50 mM Tris-acetate buffer (pH 6), 0.5 mM fructose-1,6-diphosphate, 25 mM pyruvate and 0.5 mM NADH.

The specific enzymatic activities were expressed as micromoles of converted substrate per milligram of protein per minute (equivalent to units per milligram protein).

(ix) Protein Determination

Protein content was measured by using the BCA Protein Assay Reagent (Pierce) with bovine serum albumin as the standard.

(x) Milk Fermentation

Boiled (UB) 9.5% reconstituted skim-milk (RSM) supplemented with 100 ppm of acetaldehyde and 100 ppm of diacetyl was used as fermentation substrate. The milk was inoculated with DB1334 and MW008 and samples were analysed by headspace GC every hour for twenty hours (Richelieu et al., 1997).

1.3. Results (i) Native PAGE Staining

Partially purified diacetyl reductase from *Leu. pseudomesenteroides* was separated on native gradient PAGE gels and stained with both Coomassie brilliant blue and with the zymogram technique. With the zymogram technique, the gels were incubated with diacetyl+NADH, acetoin+NADH or with butanediol+NAD$^+$. The gels were subsequently stained with Meldola's blue and MTT. With the three different incubation mixtures a protein band with the same molecular weight was visualised. In the presence of diacetyl+NADH, or with acetoin+NADH, the gel becomes saturated with NADH. However, at the position where diacetyl reductase is immobilised, the enzyme converts diacetyl+NADH into acetoin+NAD$^+$ or acetoin+NADH into butanediol+NAD$^+$. In the following incubation with Meldola's blue and MTT, these reagents react with the reduced cofactor (NADH) and the gel becomes purple except where diacetyl reductase is located. The band corresponding to diacetyl reductase becomes colourless. Incubation with butanediol and NAD$^+$ results in the reverse result. In this case, butanediol+NAD$^+$ is converted to acetoin+NADH resulting in a purple band with a colourless background. No reaction was observed with acetoin+NAD$^+$. FIG. 1 shows a native-PAGE gel incubated with different substrates and cofactors followed by staining with MTT and Meldola's blue.

(ii) Screening of EMS Mutagenized DB1334

Based on the result from the zymogram staining, an EMS mutagenized DB1334 population was screened by incubating the cells in a reaction mixture of butanediol+NAD$^+$. Lysed cells with an intact discetyl reductase (butanediol dehydrogenase activity) were stained purple whereas a diacetyl reductase (DR) mutant should become colourless Approximately 1700 clones were screened and 1 clone appeared colourless. This putative DR mutant was restreaked three times and repeatedly stained with Meldola's blue and MTT before regarded as true mutant. The selected mutant was designated MW008.

A sample of the mutant *Leu. pseudomesenteroides* MW008 strain was deposited in accordance with the Budapest Treaty with the Deutsche Sammlung vor Mikroorganismen und Zellkulturen (DSMZ), Marschenroder Weg, 1b, D-38124 Braunschweig on Apr. 7, 1998 under the Accession No. DSM 12099.

(iii) Enzyme Activity Measurements

Cell-free extracts of the DR mutant (MW008) and DB1334 were used for measuring the diacetyl reductase, butanediol dehydrogenase, acetoin reductase and lactate dehydrogenase activities. Lactate dehydrogenase activity measurements were used as a positive control for enzymatic activity of the strains. The results of the enzyme activities are summarised in Table 1.1.

TABLE 1.1

Diacetyl reductase (DR), acetoin reductase (AR), butanediol dehydrogenase (BUTDH) and lactate dehydrogenase (LDH) activities from cell free extracts of DB1334 and MW008.

| | specific activity in U/mg of protein | | | |
|---|---|---|---|---|
| strain | DR[1] | AR[1] | BUTDH[2] | LDH[1] |
| DB1334 | 2.81 | 0.81 | 0.34 | 17.70 |
| MW008 | 0.017 | n.d | n.d | 22.10 |

[1]with NADH,
[2]with NAD
n.d = not detectable, activities below the detection limit <0.005 U/mg.

1.4. Conclusions

Based on the zymogram staining of native PAGE gels containing partially purified diacetyl reductase derived from *Leu. pseudomesenteroides* it was concluded that this enzyme has activity for diacetyl+NADH, acetoin+NADH, and butanediol+NAD$^+$. No activity was observed with acetoin and NAD$^+$. Screening of a mutagenized population of *Leu. pseudomesenteroides* was performed by incubating the cells with butanediol and NAD$^+$. Alter staining, cells with an intact DR were stained purple, whereas a mutant became colourless. Cell-free extract from the DR mutant confirmed the result from the screening procedure, since essentially no activity was found with diacetyl+NADH, acetoin+NADH or butanediol+NAD$^+$.

After isolation of the NADH-dependent DR mutant, this strain was used for fermentation of milk supplemented with diacetyl and acetaldehyde. Surprisingly, the mutant strain was able to reduce diacetyl despite the absence of NADH-dependent diacetyl reductase activity. Measurements of cell free extract of the mutant with diacetyl+NADPH, acetoin+NADPH and butanediol+NADP$^+$ showed similar activities as the wild type. Therefore, it was most likely that DB1334 has two diacetyl reductases responsible for diacetyl degradation. In order to prevent diacetyl reduction during milk fermentation, also the NADPH-dependent diacetyl reductase of DB1334 must be mutated.

EXAMPLE 2

Demonstration of both NADH- and NADPH-dependent Diacetyl Reductase Activities in *Leuconostoc pseudomesenteroides* and Construction of Mutant Strains Totally Blocked in Diacetyl Reductase Activities 2.1. Summary of Experiments In Example 1 the construction of a diacetyl reductase mutant with no essentially activity for diacetyl+NADH is described. However, the mutant possessed diacetyl reductase activities as the wild-type strain when using NADPH as cofactor. This strain was able to degrade diacetyl at the same rate as the wild-type strain. The NADH-dependent diacetyl reductase mutant was subjected to further mutagenization and screened for mutants incapable of reducing diacetyl both in the presence of NADH and NADPH as cofactors 2.2. Materials and Methods (ii) Bacterial Strains

*Leuconostoc pseudomesenteroides* DB1334 (CHCC2114), MW008 (NADH-dependent diacetyl reductase mutant, see Example 1) and MM0084 (NADH-, NADPH-dependent diacetyl reductase mutant, this Example).

(ii) Cultivation Conditions

DB1334, MW008 and MM084 were cultivated on M17 (0.5% glucose) plates, or in liquid medium, at 25° C. under anaerobic conditions.

(iii) Mutagenesis

MW008 was cultivated in 10 ml M17 (0.5% glucose) for three days followed by cultivation for 120 minutes in the presence of 150 μl of EMS. After EMS treatment, monitored by plating 0.1 ml from each tube on M17 plates containing 500 μg/ml of streptomycin.

(iv) Colony Screening

Mutated cells were plated on M17 (0.5% glucose) and incubated for 2 days at 25° C. anaerobically and streaked onto duplicate M17 plates. After another 2 days of incubation one of the duplicate plates was used for screening. The colonies were transferred onto a nitrocellulose membrane and soaked for 1.5 minutes in chloroform for cell lysis. After cell lysis, the membrane was washed with distilled water and dried for 20 minutes. The membrane was subsequently incubated for 30 minutes in a solution containing; 0.5 M Na-phosphate buffer (pH 6.1), 72 mM butanediol, 1 mM $NAD^+$ or $NADP^+$, 0.02 mM Meldola's blue (8-Dimethylamino-2,3-benzophenoxazine), 0.08 mM MTT (3-[4,5-Dimethylthiazol-2yl] 2,5-diphenyltetrazolium bromide; Thiazolyl blue).

(v) Protein Electrophoresis

Native-PAGE was run at 150 V for 2.5 hours using 4–20% Tris-HCl gradient gels with Tris-Glycine (pH 8.3) as running buffer. Staining of native gels was performed with the zymogram technique (see below).

(vi) Zymogram Staining of Gels

Zymogram staining of native-PAGE gels for identification of diacetyl reductase activity, acetoin reductase activity and butanediol dehydrogenase activity was performed as follows: for diacetyl reductase activity the gel was incubated for 15 minutes with 12 mM diacetyl, 1.5 mM NADH or NADPH, 0.5 M Na-phosphate buffer (pH 6.1), for acetoin reductase activity the gal was incubated for 15 minutes with 36 mM acetoin, 1.5 mM NADH or NADPH, 0.5 M Na-phosphate buffer (pH 6.1) and for butanediol dehydrogenese activity the gel was incubated for 15 minutes with 72 mM butanediol. 1 mM $NAD^+$ or $NADP^+$, 0.5 M Na-phosphate buffer. The gel was next incubated for 30 minutes under dry conditions before the addition of a solution consisting of 0.02 mM Meldola's blue (8-Dimethylamino-2,3-benzophenoxazine), 0.08 mM MTT (3-[4.5-Dimethylthiazol-2yl] 2,5-diphenyltetrazolium bromide; Thiazolyl blue) in 100 mM phosphate buffer (pH 8.2) (Provecho et al, 1984; Gibson et al, 1991). Visible protein bands appeared within 20 minutes (vii) Cell-free Extracts DB1334, MW008 and MM084 were cultivated in M17 (0.5% glucose) until mid exponential phase. The cells were harvested by centrifugation at 6000 rpm for 15 minutes and washed in cold 50 mM Na-phosphate buffer (pH 6). The pellet was resuspended in cold 50 mM Na-phosphate buffer (pH 6) and sonicated for 3×2 minutes. The sonicated cell mixture was centrifuged at 6000 rpm for 15 minutes and the supernatant was stored at −20° C. until analysed for protein concentration and enzyme activities.

(vii) Enzyme Activity Measurements

Diacetyl reductase activity was measured spectrophotometrically by monitoring the oxidation of NADH or NADPH at 340 nm in a reaction mixture with the following composition: 50 mM Na-phosphate buffer (pH 6.1), 36 mM diacetyl and 0.5 mM NADH or NADPH. Butanediol dehydrogenase activity was measured spectrophotometrically by monitoring the reduction of $NAD^+$ or $NADP^+$ at 340 nm in a reaction mixture with the following composition: 50 mM Naphosphate buffer (pH 6.1), 72 mM butanediol and 0.5 mM $NAD^+$ or $NADP^+$. Acetoin reductase activity was measured spectrophotometrically by monitoring the oxidation of NADH or NADPH at 340 nm in a reaction mixture with the following composition: 50 mM Na-phosphate buffer (pH 6.1), 36 mM acetoin and 0.5 mM NADH or NADPH. Lactate dehydrogenase activity was measured by monitoring the oxidation of NADH at 340 nm in a reaction mixture with the following composition: 50 mM Tris-acetate buffer (pH 6), 0.5 mM fructose-1,6-diphosphate, 25 mM pyruvate and 0.5 mM NADH. The specific activities of the enzymes were expressed as micromoles of converted substrate per milligram of protein per minute (equivalent to units per milligram protein).

(viii) Protein Determination

Protein concentration was measured by using the BCA Protein Assay Reagent (Pierce) with bovine serum albumin as the standard.

2.3. Results (i) Screening of EMS Mutagenized MW008

Based on the previous results that diacetyl reductase is also able to react with butanediol and $NADP^+$ (see Example 1), mutagenized MW008 was screened by incubating the cells in a solution consisting of butanediol and $NADP^+$. Possible mutants were colourless whereas cells with an intact diacetyl reductase were stained purple. Approximately 3500 clones were screened with the zymogram method. Two possible mutants were further restreaked three times and repeatedly restrained with Meldola's blue and MTT. One of the two possible clones was found to be an NADPH-dependent diacetyl reductase mutant. This clone was designated MM084.

A sample of the mutant Leu. pseudomesenteroides MM084 strain was deposited in accordance with the Budapest Treaty with the Deutsche Sammlung von Mikroorganismen und Zellkulturen (DSMZ), Marschenroder Weg, 1b, D-38124 Braunschweig on Oct. 28, 1998 under the Accession No. DSM12465.

(ii) Enzyme Activity Measurements

Cell free extracts of DB1334, MW008 and MM084 were used for measuring diacetyl reductase, acetoin reductase and butanediol dehydrogenase activities. As a positive control for the activity of the strains, lactate dehydrogenase activity was also measured. The enzyme activities of DB1334, MW008 and MM084 are summarised in Table 2.1. Values for lactate dehydrogenase activities of the mutants were comparable to the wild-type strain (data not shown).

TABLE 2.1

Diacetyl reductase (DR), acetoin reductase (AR), and butanediol dehydrogenase (BUTDH) activities from cell free extracts of DB1334, MW008, and MM084.

| | specific activity (U/mg) | | | | | |
| --- | --- | --- | --- | --- | --- | --- |
| | DR | | AR | | BUTDH | |
| strain | NADH | NADPH | NADH | NADPH | $NAD^+$ | $NADP^+$ |
| DB1334 | 2.81 | 1.47 | 0.81 | 0.77 | 0.34 | 0.16 |
| MW008 | 0.017 | 1.27 | n.d | 0.84 | n.d | 0.14 |
| MM084 | n.d | n.d | n.d | n.d | n.d | n.d | n.d = not detectable, activities below the detection limit <0.005 U/mg.

(iii) Zymogram Stained Native-PAGE Gels

Native-PAGE gels run with cell extracts from DB1334 and MM084 and incubated with diacetyl+NADPH, and butanediol+$NADP^+$ showed that MM084 possessed no activities with these substrates and cofactors (FIG. 2).

2.4. Conclusions

It has been shown that wild-type Leu. pseudomesenteroides is capable of reducing diacetyl into acetoin and butanediol due to diacetyl reductase activities using either NADH or NADPH as cofactors.

An NADH-dependent diacetyl reductase mutant was capable of reducing diacetyl at the same rate as that of the wild-type strain during milk fermentation. When using NADPH as cofactor, the mutant had enzyme activities comparable to the wild-type strain. Mutagenesis and screening of MW008 with the zymogram technique resulted in the isolation of an NAD(P)H-dependent diacetyl reductase mutant. Such a mutant would be incapable of reducing diacetyl into acetoin end butanediol by means of diacetyl reductese.

EXAMPLE 3

Effect of Diacetyl Reductase Deficient *Leuconostoc pseudomesenteroides* Strain MM084 on Diacetyl Stability in Fermented Dairy Products Under Storage 3.1. Introduction As described in Example 2, the diacetyl reductase mutant MM084 is isolated as a double mutant of *Leuconostoc pseudomesenteroides* strain DB1334 and lacks both NADH and NADPH dependent DR.

When cultivated in milk as a pure culture, MM084 does not reduce diacetyl and acetoin. Due to this characteristic, mutant MM084 is assumed to be a suitable strain for use as a component in mesophilic cultures which results in an improved diacetyl stability in the fermented products. In this Example, the effect of the mutant MM084 on flavour formation and stability in fermented milk was investigated with main focus on the concentration of diacetyl.

3.2. Materials and Methods (i) Bacterial Strain

The strains used in this example originate from the Chr. Hansen Culture Collection:

*Lactococcus lactis* subsp. *lactis* DB1387 (O strain);
*Lactococcus lactis* subsp. *lactis* biovar. *diacetylactis* strain DB1341 (D strain);
*Lactococcus lactis* subsp. *lactis* biovar. *diacetylactis* -acetolactase decarboxylase deficient mutant MC010 (Curic et al. 1999) (D strain);
*Leuconostoc pseudomesenteroides* DB 1334 (L strain);
*Leuconostoc pseudomesenteroides* DR mutant MM084 (L strain).

Mixed cultures were composed of three different strains. Strains were produced as frozen pellets and stored at −50° C. The prepared inoculum contained $1.5 \times 10^8$ CFU/ml.

The following mixed culture were used in this example:
A) DB1387+DB1341+DB1334
B) D1387+DB1341+MM084
C) DB1387+MC010+D1334
D) DB1387+MC010+MM084
Mixed culture A and C were used as a control.

(ii) Cultivation Medium

Reconstituted skimmed milk (9.5%); 200 ml in 250 ml bottles. Cream: Commercially available dairy cream (13%) was adjusted to 11% fat by addition of skimmed milk, distributed in 500 ml bottles, re-pasteurised at 85° C. for 30 min and cooled to 22° C. prior to inoculation.

(iii) Cultivation Conditions

The milk of cream was inoculated with a total of 1% of inoculum and incubated at 22° C. until pH reached 4.60±0.05. Following incubation, the bottles were kept at 4° C.

(iv) Determination of Fermentation Product Formation

Samples for analyzing the product formation were taken immediately after inoculation, during fermentation and during storage. Concentrations of the volatile compounds ethanol, acetaldehyde, -acetolactate, acetoin and diacetyl were determined by HSGC (Richelieu et al., 1997).

3.3 Results and Discussion

No significant differences in the acidification rate were observed between milk fermented with cultures containing DR MM084 (B and D) and the control mixed cultures (A and C) (results not shown). At the end of the fermentation, all four mixed cultures produced similar amounts of ethanol and acetaldehyde. In all mixed cultures except culture D, acetaldehyde was reduced until the end of the fermentation (results not shown). Excess of acetaldehyde may cause yoghurt-like flavour of buttermilk, which is considered as an off-flavour. However, the concentration of acetaldehyde with mixed culture D is reduced during the first 2–3 days of storage.

It is shown that reduction of the diacetyl reductase activity of the Leuconostoc strain MM084 has a significant effect on the stability of diacetyl during storage (Tables 3.1 and 3.2, FIG. 3 and 4). The diacetyl content in the medium at the end of the fermentation is significantly higher in mixed cultures containing MM084 (B and D) as compared to the control mixed cultures (A and C).

TABLE 3.1

Diacetyl concentrations in milk, fermented by the mixed cultures A and B, during fermentation and storage.

| | | Diacetyl (mg/L) | |
|---|---|---|---|
| | Time (h) | Mixed culture A | Mixed culture B |
| Fermentation | 0 | 0.0 | 0.0 |
| | 13 | 0.3 | 0.3 |
| | 15 | 1.2 | 0.1 |
| | 17 | 2.0 | 1.1 |
| | 19 | 1.8 | 1.4 |
| | 21 | 1.0 | 1.6 |
| | 22 | 0.5 | 1.4 |
| Storage | 46 (+1 day) | 0.3 | 0.9 |
| | 94 (+3 days) | 0.2 | 0.8 |
| | 142 (+5 days) | 0.0 | 0.7 |
| | 190 (+7 days) | 0.0 | 0.6 |
| | 358 (+14 days) | 0.0 | 0.6 |
| | 502 (+20 days) | 0.0 | 0.7 |

TABLE 3.2

Diacetyl concentrations in sour cream fermented by the mixed cultures C and D during fermentation and storage.

| | | Diacetyl (mg/L) | |
|---|---|---|---|
| | Time (h) | Mixed culture C | Mixed culture D |
| Fermentation | 0 | 0.0 | 0.0 |
| | 12 | 3.7 | 2.3 |
| | 13 | 5.5 | 4.6 |
| | 14 | 7.1 | 9.7 |
| | 15 | 9.4 | 12.8 |
| | 16 | 8.5 | 12.4 |
| | 17 | 8.0 | 9.6 |
| Storage | 41 (+1 day) | 1.9 | 5.4 |
| | 113 (+4 days) | 0.5 | 4.6 |
| | 161 (+6 days) | 0.6 | 4.2 |
| | 305 (+12 days) | 0.3 | 2.0 |
| | 689 (+28 days) | 0.1 | 0.8 |
| | 857 (+35 days) | 0.1 | 0.9 |
| | 1025 (+42 days) | 0.1 | 1.0 |

The sour cream fermented with the cultures C and D was sensorically evaluated after 1, 7, 14, 21, and 28 days, respectively. The sour cream had a mild, clean and fresh flavour. The fresh flavour was maintained during a prolonged storage.

3.4. Conclusion

The strain MM084 is suitable for use as a component of a mixed aroma-forming culture. The mixed cultures composed with MM084 had a significantly improved diacetyl stability during storage and a significant higher content of diacetyl at the end of fermentation and after storage. Such a mixed culture is beneficial in the production of sour cream and cream cheeses.

EXAMPLE 4

Isolation and Characterisation of a *Lactococcus latcis* subsp. *lactis* Mutant with Enhanced Diacetyl Reductase Activity

4.1. Introduction

The *L. lactis* subsp. *lactis* mutant strain DN223 is both a lactate dehydrogenase (LDH) and pyruvate formate lyase (PFL)defective. DN223 is strictly aerobic and the lack of capability to grow anaerobically (even in the presence of acetate) is most likely due to a constraint on the intracellular redox balance, as the net consumption of $NAD^+$ in the glycolysis can no longer be regenerated due to the two enzymatic defects. Exogenous acetoin was expected to assist in the regeneration of $NAD^+$ under anaerobic conditions by conversion into 2,3-butanediol by the enzyme diacetyl reductase (DR).

4.2. Isolation of a Mutant with Enhanced DR Activity

A test tube containing 10 ml of DN medium (Dickely et al., 1995) supplemented with acetate was inoculated with a single colony of DN223 picked from an agar plate and incubated aerobically overnight at 30° C. 100 µl of the overnight culture was spread onto two agar plates containing DN medium supplemented with 2.0 g/L sodium acetate trihydrate and 0.5 g/L acetoin and incubated anaerobically for two days at 30° C. A number of colonies were subsequently streaked onto agar plates containing DN medium supplemented with acetate and with and without 0.5 g/l acetoin and incubated anaerobically for two days at 30° C. One mutant designated CMH-153 was isolated which only displayed anaerobic growth if the medium was supplemented with 0.5 g/L acetoin.

A sample of the *L. lactis* subsp. *lactis* CMH-153 strain was deposited in accordance with the Budapest Treaty with the Deutsche Sammlung vor Mikroorganismen und Zellkulturen (DSMZ), Marschenroder Weg, 1b, D-38124 Braunschweig on Apr. 7, 1998 under the Accession No. DSMA 12096.

4.3. Characterisation of *L. lactis* CMH-153

200 ml of DN medium supplemented with acetate was inoculated with a single colony of CMH-153 picked from an agar plate and incubated aerobically overnight at 30° C. Subsequently, a cell-free extract was made and the protein content of the extract was measured.

The diacetyl activities of strain CMH-153 were measured with diacetyl as substrate and NADH as cofactor and are expressed as the units of [µmoles NADH consumed per min. per mg of protein] according to the assay described in Example 1. The diacetyl activities of strain CMH-153 were compared with other *L. lactis* subsp. *lactis* strains (Table 4.1).

Additionally, the diacetyl activities of strain CHM-153 were measured using either diacetyl, acetoin or 2,3-butanediol as substrate and NADH, $NAD^+$, NADPH or NADP+ as cofactor and are expressed as units of [µmoles NADH or NADPH produced or consumed per min per mg of protein] according to the assay described in Example 1. The diacetyl activities of strain CMH-153 were compared with other *L. lactis* subsp. *lactis* strains (Table 4.2).

TABLE 4.1

Diacetyl reductase activity of CMH-153 compared with other *L. lactis* subsp. *lactis* strains.

| Strain | Phenotype | Specific activity |
|---|---|---|
| CHCC373 | Wild-type | n.d. |
| DN221 | Pfl⁻ | n.d. |
| DN223 | Pfl⁻/Ldh⁻ | 0.01–0.02 |
| DN224 | Ldh⁻ | 0.01 |
| CMH-153 | Pfl⁻/Ldh⁻/Dr⁺⁺ | 0.92 | n.d = not detectable, activities below the detection limit <0.005 U/mg.

TABLE 4.2

Diacetyl reductase activity of CMH-153 compared with other *L. lactis* subsp. *lactis* strains

| | | Strains | | |
|---|---|---|---|---|
| Enzymatic reaction | Co-factor | CHCC373 | DN223 | CMH-153 |
| diacetyl ---> acetoin | NADH | n.d | n.d. | 1.15 |
| | NADPH | n.d. | n.d. | 0.04 |
| acetoin ---> diacetyl | $NAD^+$ | n.d. | n.d. | n.d. |
| | NADP⁺ | n.d. | n.d. | n.d. |
| acetoin ---> 2,3-butanediol | NADH | 0.02 | 0.07 | 0.41 |
| | NADPH | n.d. | n.d. | 0.02 |
| 2,3-butanediol ---> acetoin | $NAD^+$ | n.d. | n.d. | 0.12 |
| | NADP⁺ | n.d. | n.d. | n.d. | n.d = not detectable, activities below the detecton limit <0.005 U/mg.

Finally, the specific LDH activity of strain CMH-153 was measured using the method as also described in Example 1 and compared with other *L. lactis* subsp. *lactis* strains (Table 4.3). Activities are expressed as units of [µmoles NADH consumed per min. per mg of protein].

TABLE 4.3

Lactate dehydrogenase activity of CMH-153 compared with other *L. lactis* subsp. *lactis* strains

| Strain | Phenotype | Specific activity |
|---|---|---|
| CHCC373 | Wild-type | 15.3 |
| DN221 | Pfl⁻ | 15.3 |
| DN223 | Pfl⁻/Ldh⁻ | n.d. |
| DN224 | Ldh⁻ | n.d. |
| CMH-153 | Pfl⁻/Ldh⁻/Dr⁺⁺ | n.d. | n.d = not detectable, activities below the detection limit <0.005 U/mg.

The specific diacetyl reductase activities of CMH-153 are significantly increased compared to other *L. lactis* strains with various phenotypes (Table 4.1 and 4.2) whereas CMH-1 53 has no detectable LDH activity (Table 4.3). Thus, the mutant strain *L. lactis* subsp. *lactis* CMH-153 has the phenotype Ldh⁻/Pfl⁻/Dr⁺⁺, as it is only capable of anaerobic growth if supplied with acetoin and acetate.

REFERENCES

Arora, B. C., Dutta, S. M., Sabharwal. V. B. and Rangenathan, B. (1978). Mutants of *Streptococcus lactis* subsp. *diacetylactis* lacking diacetyl reductase activity. Acta Microbiol Pol 27:353–358.

Boumerdassi, H., Monnet, C., Desmazeaud and M., Corrieu, G. (1997). Isolation and properties of *Lactococcus lactis* subsp. *lactis* biovar *diacetylactis* CNRZ 483 mutants producing diacetyl and acetoin from glucose. Appl. Environ. Microbiol. 63: 2293–2299.

Crow, V. L. (1990). Properties of 2,3-butanediol dehydrogenases from *Lactococcus lactis* subsp. *lactis* in relation to citrate fermentation. Appl. Environ. Microbiol. 56:1656–1665.

Curic, M., Lauridsen, B. S., Renault, P. and Nilsson. D. (1999). A general method for selection of -acetolactate decarboxylase deficient *Lactococcus lactis* mutants to improve diacetyl formation. Appl. Environ. Microbiol. 63:1202–1206.

Dickely, F., Nilsson, D., Hansen, E. B. and Johansen, E. (1995). Isolation of *Lactococcus lactis* nonsense suppressors and construction of a food-grade cloning vector. Mol. Microbiol. 15:839–847.

Gibson, T. D., Parker, S. M. and Woodward, J. R. (1991). Purification and characterization of diacetyl reductase from chicken liver and *Streptococcus lactis* and enzymatic determination of diacetyl and ketones. Enz. Microb. Technol. 13:171–178.

Giovannin, P. P., Medici, A, Bergamini, C. M. and Rippa, M. (1996). Properties of diacetyl (acetoin) reductase from *Bacillus stearothermophilus*. Bioorg. Med Chem. 4:1197–1201.

Kulia, R. K. and Ranganathan, B. (1978). Ultraviolet light-induced mutants of *Streptococcus lactis* subsp. *diacetylactis* with enhanced acid- or flavor-producing abilities. J. Dairy Sci. 61:379–383.

Provecho, F., Burgos, J. and Sarmiento, R. M. (1984). Further purification and characterization of diacetyl reducing enzymes from beef liver. Int. J. Biochem. 16:423–427.

Richelieu, M., Houlberg, U. and Nielsen, J. C. (1997). Determination of α-acetolactic acid and volatile compounds by headspace gas chromatography. J. Dairy Sci. 80:1918–1925.

Terzaghi, B. E. and Sandine, W. E. 1975). Improved medium for *Lactic streptococci* and their bacteriophages. Appl. Microbiol. 29:807–813.

What is claimed is:

1. A genetically modified lactic acid bacterium of a Leuconostoc species that, relative to the lactic acid bacterium from which it is derived, is modified to have a reduction of at least 25% of diacetyl reductase activity, acetoin reductase activity and butanediol dehydrogenase activity in the presence of NADH, NADPH, NAD+ or NADP+.

2. A bacterium according to claim 1 which is of *Leuconostoc pseudomesenteroides*.

3. A bacterium according to claim 2 which is selected from the group consisting of *Leuconostoc pseudomesenteroides* strain DSM 12099, a *Leuconostoc pseudomesenteroides* strain having the diacetyl reductase activity, acetoin reductase activity and butanediol dehydrogenase activity of DSM 12099, DSM 12465 and a *Leuconostoc pseudomesenteroides* strain having the diacetyl reductase activity, acetoin reductase activity and butanediol dehydrogenase activity of DSM 12465.

4. A bacterium according to claim 1 which is modified to have, in the presence of NADH and NADPH, a reduction of at least 25% of diacetyl reductase activity, acetoin reductase activity and butanediol dehydrogenase activity.

5. A bacterium according to claim 1 which is modified to have a reduction of at least 90% of diacetyl reductase activity, acetoin reductase activity and butanediol dehydrogenase activity.

6. A bacterium according to claim 1, where the bacterium prior to being modified has diacetyl reductase activity, acetoin reductase activity and butanediol dehydrogenase activity, substantially lacks said enzymatic activities in the presence of NADH, NADPH, NAD+, or NADP+.

7. A bacterium according to claim 6 that lacks diacetyl reductase activity and acetoin reductase activity in a medium containing NADH and not containing NADPH.

8. A bacterium according to claim 6 that substantially lacks diacetyl reductase activity and acetoin reductase activity in a medium containing NADPH and not containing NADH.

9. A bacterium according to claim 6 that substantially lacks diacetyl reductase activity and acetoin reductase activity in a containing both NADH and NADPH.

10. A bacterium according to claim 6 that substantially lacks butanediol dehydrogenase activity in a medium containing NAD+ and not containing NADP+.

11. A bacterium according to claim 6 that substantially lacks butanediol dehydrogenase activity in a medium containing NDAP+ and not containing NAD+.

12. A bacterium according to claim 6 that substantially lacks butanediol dehydrogenase activity in a medium containing both NAD+ and NADP+.

13. A bacterium according to claim 1 that is derived by subjecting a parent lactic acid bacterial strain that in the presence of NADH, NADPH, NAD+, or NADP+ has diacetyl reductase activity, acetoin reductase activity and butanediol dehydrogenase activity to a chemical mutagen or ultraviolet light and selecting a strain that substantially lacks said enzymatic activities in the presence of NADH, NADPH, NAD+, or NADP+.

14. A starter culture composition comprising said genetically modified lactic acid a bacterium according to claim 1.

15. A composition according to claim 14 that is a frozen, dried or freeze-dried composition.

16. A composition according to claim 15 containing a viable amount of said genetically modified lactic acid bacteria which is in the range of $10^4$ to $10^{12}$ cfu per g.

* * * * *